United States Patent [19]

Januszewski et al.

[11] 3,989,813

[45] Nov. 2, 1976

[54] STABILIZED DENTIFRICE

[75] Inventors: Joseph Paul Januszewski, Somerville, N.J.; Tayseer George Balhouth, deceased, late of Piscataway, N.J., by Zaher G. Balhouth, administrator, Utica, N.Y.

[73] Assignee: Colgate-Palmolive Company, New York, N.Y.

[22] Filed: Oct. 9, 1975

[21] Appl. No.: 621,179

Related U.S. Application Data

[63] Continuation of Ser. No. 326,810, Jan. 26, 1973, abandoned, which is a continuation of Ser. No. 126,971, March 22, 1971, abandoned, which is a continuation-in-part of Ser. No. 818,084, April 21, 1969, Pat. No. 3,641,238.

[52] U.S. Cl. .................................. 424/54; 424/57
[51] Int. Cl.$^2$ .......................................... A61K 7/22
[58] Field of Search ............................... 424/49–58

[56] References Cited

UNITED STATES PATENTS 3,842,168   10/1974   Colodney ............................ 424/52

*Primary Examiner*—Shep K. Rose
*Attorney, Agent, or Firm*—Robert L. Stone; Murray M. Grill; Herbert S. Sylvester

[57] ABSTRACT

Dentifrice containing flavoring oil and phosphate ion and 1,6-di-(p-chlorophenyl biguanidohexane) and ethanol to stabilize the dentifrice against separation.

5 Claims, No Drawings

STABILIZED DENTIFRICE

This is a continuation of application Ser. No. 326,810 filed Jan. 26, 1973, now abandoned, which is a continuation of Ser. No. 126,971 filed 3/22/71, now abandoned, which is a continuation-in-part of Ser. No. 818,084 filed 4/21/69, now U.S. Pat. No. 3,641,238, issued 2/8/72.

This invention relates to stabilization of a dentifrice composition. More particularly, it relates to stabilization of a dental cream composition which promotes oral hygiene.

The dentifrice of the instant invention contains a highly desirable antibacterial agent, 1,6-di-(p-chlorophenyl biguanidohexane) as the free base or as a non-toxic acid addition salt thereof. This antibacterial agent is known to possess highly desirable effect in inhibiting the growth of many microorganisms such as *Lactobacillus acidophilus odontolyticus* and has, therefore, been recommended for incorporation into dentifrices.

However, the cosmetic stabilities of many dentifrices including this antibacterial agent have not been satisfactory particularly in view of the tendency of such dentifrices to separate into liquid and solid phases.

It is an advantage of the instant invention that a stable dentifrice including 1,6-di-(p-chlorophenyl biguanidohexane) is provided. Other advantages of the invention will be apparent from consideration of the following specification.

In accordance with certain of its aspects, this invention relates to a dentifrice comprising 1,6-di-(p-chlorophenyl biguanidohexane), in amount to provide about 0.01–5% by weight of the free base, and a dentifrice vehicle comprising solids and liquids and containing about 0.5–5% by weight of flavoring oil and phosphate ion in amount of about 0.015–2% by weight, and, as an agent to stabilize said dentifrice against separation, about 2.5–5.0% of ethanol.

1,6-di-(p-chlorophenyl biguanidohexane) may be employed in the instant invention in the form of its free base or its non-toxic acid addition salts, such as the water-soluble gluconate, acetate, fluoride, dihydrogen fluoride and the like. As used herein, the compound named refers to the free base as well as the acid-addition salt thereof, unless otherwise specified. The antibacterial agent is present in amounts ranging from about 0.01–5% by weight, preferably about 0.05–1.0%, of the dentifrice. These amounts refer to the quantity of free base present.

The antimicrobial agent is incorporated into a vehicle of a dentifrice such as a toothpaste or dental cream. The vehicle typically contains a dentally acceptable substantially water-insoluble polishing agent, a liquid which may be water or a humectant, a gelling agent, and flavoring oil. It may also include additional components such as synthetic organic surface-active agents, additional antibacterial agent, sweetener, dentally beneficial fluorine-containing compound, an ion-suppressing agent as well as coloring or whitening agents, preservatives, silicones, chlorophyll compounds, ammoniated compounds and the like.

Any suitable substantially water-insoluble dentally acceptable polishing agent may be employed in the preparation of dentifrice compositions, such as toothpastes or creams and the like, in accordance with the present invention. There is a relatively large number of such materials known in the art. Representative agents include, for example, dicalcium phosphate, dimagnesium orthophosphate, tricalcium phosphate, insoluble sodium metaphosphate, aluminum hydroxide, crystalline silica, magnesium carbonate, calcium carbonate, calcium pyrophosphate, bentonite, etc., including suitable mixtures thereof. It is often desired to use the substantially water-insoluble phosphate salts as the polishing agents, and, more particularly, insoluble sodium metaphosphate. In dentifrices containing 1,6-di-(p-chlorophenyl biguanidohexane), aluminum hydroxide, such as the hydrated alumina sold by Alcoa as C333, and crystalline silica polishing agents are also highly desirable. Since polishing agents such as insoluble sodium metaphosphate and calcium and magnesium phosphates contain a soluble portion, the amounts in which they are used should not provide more than about 2% by weight of phosphate ion to the dentifrice.

The polishing agent content is variable, but will generally be up to about 75% by weight of the total composition, typically about 20–75%.

In dentifrice vehicles of formulations such as toothpastes and dental creams, liquids and solids should necessarily be proportioned to from a creamy or gelled mass of desired consistency which is extrudable from an aerosol container or a collapsible, eg., aluminum or lead, tube. In general, the liquids in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20–75% by weight of the formulation. It is preferred to use also a gelling agent in dental creams such as the natural and synthetic gums and gum-like materials, e.g., Irish moss, gum tragacanth, methyl cellulose, hydroxyethyl cellulose, sodium carboxymethyl cellulose, polyvinylpyrrolidone, Laponite CP or SP, which are each synthetic inorganic complex silicate clays sold under trademark by Laporte Industries Ltd., and starch, usually in an amount up to about 10%, and preferably about 0.2–5% of the formulation. The preferred gelling agents are sodium carboxymethyl cellulose, methyl cellulose and hydroxyethyl cellulose. If sodium carboxymethyl cellulose is employed, preferably the dentifrices are formed in accordance with the technique described in U.S. Pat. No. 3,842,168 of Daniel Colodney and U.S. Pat. No. 3,843,779 of James Norfleet.

Organic surface-active agents used in the compositions of the present invention to achieve increased prophylactic action, assist in achieving thorough and complete dispersion of the instant compositions throughout the oral cavity, and render the instant compositions more cosmetically acceptable. When an anionic surface-active material is desired, substantially saturated higher aliphatic acyl amides of lower aliphatic amino, carboxylic acid, compounds such as those having 12 to 16 carbons in the fatty acid, alkyl or acyl radicals are particularly preferred. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these material exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol (available under the trademark "Pluronics") and amphoteric agents such as quaternized imidazole derivatives which are available under the trademark "Miranol" such as Miranol $C_2M$. Cationic surface-active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethanoxy groups per molecule) and salts thereof with acids and compounds of the structure

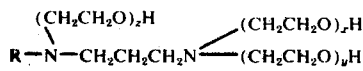

where R is a fatty alkyl group containing from about 12 to 18 carbon atoms, and $x$, $y$ and $z$ total 3 or higher, as well as salts thereof with mineral or organic acids, may also be used. It is preferred to use from about 0.05 to 5% by weight of the foregoing surface-active materials in the instant oral preparations.

Various other materials may be incorporated in the oral preparations of this invention. Examples thereof are coloring or whitening agents, preservatives, silicones, chlorophyll compounds, ammoniated materials such as urea diammoniumphosphate and mixtures thereof, and other constituents. These adjuvants are incorporated in the instant compositions in amounts which do not substantially adversely affect the properties and characteristics desired and are selected and used in proper amount depending upon the particular type of preparation involved. For example, ammoniated materials such as urea, diammonium phosphate and mixtures thereof, when present, are typically employed in amount of about 1 to 2% by weight.

In addition to 1,6-di-(p-chlorophenyl biguanidohexane), dentifrices in accordance with this invention may include additional cationic antibacterial agents such as
- $N^1$-(4-chlorobenzyl)-$N^5$-(2,4-dichlorobenzyl)biguanide
- p-chlorophenyl biguanide
- 4-chlorobenzyhydryl biguanide;
- 4-chlorobenzhydrylguanylurea;
- N-3-lauroxpropyl-$N^5$-p-chlorobenzylbiguanide;
- 1-(lauryldimethylammonium)-8-(p-chlorobenzylidimethylammonium) octane dichloride;
- 5,6-dichloro-2-guanidinob nzimidazole;
- $N^3$-p-chlorophenyl-$N^5$-laurylbiguanide;
- 5-amino-1,3-bis (2-ethylhexyl)-5-methylhexahydropyrimidine;

and their non-toxic acid addition salts such as the gluconate and acetate. The total amount of such agents including 1,6-di-(p-chlorophenyl biguanidohexane) is typically about 0.05%–5% by weight.

The dentifrice vehicle of the instant invention contains a flavoring oil and may also contain a sweetening agent. Examples of suitable flavoring oil include oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and saccharine. Suitably, flavor alone or together with sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2.KF$), sodium hexaflurostannate, stannous chlorofluoride, sodium fluorozirconate, and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The dentifrices should have a pH practicable for use. The pH range of about 5 to 9, preferably about 6–7, is considered the most practicable for use. Where reference is made to pH herein, it is intended that such pH determination be made on the dentifrice directly.

In the event the dentifrice vehicle contains as polishing agent a water-insoluble calcium or magnesium salt, there may be employed also various calcium and magnesium ion suppression agents for adjustment of physical properties of the composition. Suitable agents are the water-soluble inorganic polyphosphate salts, such as tetrasodium pyrophosphate or disodium diacid pyrophosphate, with the partially neutralized or acid polyphosphates preferred. In general, such compounds will be a minor amount or proportion of the formulation. The precise amount will vary depending upon the specific formulation, such as the physical characteristics of the dental cream, but will usually be from about 0.1% to about 2% by weight.

When the dentifrice containing 1,6-di-(p-chlorophenyl biguanidohexane) includes a material which provides phosphate ion (i.e., orthophosphate, metaphosphate and polyphosphate, such as pyrophosphate, ion) and a flavoring oil the paste separates into liquid and solid phases. The phosphate ion may be provided from the small amount of substantially water-insoluble polishing agent, such as insoluble sodium metaphosphate, dicalcium orthophosphate, dimagnesium orthophosphate, tricalcium phosphate, calcium pyrophosphate and the like which is solubilized in the paste. It may also be provided from the agent which suppresses solubility of sustantially water-insoluble calcium or magnesium polishing agents such as tetrasodium pyrophosphate or disodium diacid pyrophosphate, from ammoniated materials such as diammonium phosphate as well as other sources. As little as about 0.015% by weight of phosphate ion in the dentifrice together with flavoring oil and 1,6-di-(p-chlorophenyl biguanidohexane) results in separation of the dentifrice. Generally, the dentifrice is stabilized in the presence of stabilizers even with a phosphate ion content of about 2% by weight.

It has been observed that separation occurs even if the dentifrice containing 1,6-(p-chlorophenyl biguanidohexane), phosphate ion and flavoring oil also includes hydrated alumina which has been previously disclosed, particularly in minor amounts, to prevent separation and bleeding of dentifrices.

In accordance with the instant invention, separation of the above-described dentifrices is substantially prevented by incorporating into the dentifrice a minor amount such as about 2.5–10% by weight, preferably about 1–5% and most preferably about 2.5%–5%, of ethanol.

In our above-mentioned application Ser. No. 818,084 of which this application is a continuation-in-part, we described a dentifrice in which ethanol was employed to prevent separation of dentifrices containing polishing agent, benzyl alcohol and oil of cloves. In this dentifrice, the phosphate ion could be present from the polishing agent or from other sources, and 1,6-di-(p-chlorophenyl biguanidohexane) could be optionally present.

In the instant aspect of the invention, it is shown that in the presence of 1,6-di-(p-chlorophenyl biguanidohexane) separation which takes place when phosphate ion and oil of cloves or other flavoring oils are also present, even if benzyl alcohol is omitted, is also substantially prevented by ethanol.

The following specific example is further illustrative of the nature of the present invention, but it is understood that the invention is not limited thereto. The compositions are prepared as indicated and all amounts and proportions are by weight unless otherwise specified.

EXAMPLE 1

The following dentifrice is prepared in accordance with the technique described in Example 1 of the above-referred to U.S. Pat. No. 3,842,168 of Daniel Colodney:

|  | Parts |  |
|---|---|---|
| 1,6-di-(p-chlorophenyl biguanidohexane) digluconate | 0.5 | (Free Base) |
| Ethanol (95% by volume) | 5.0 | |
| Vehicle | | |
| Glycerine | 22.0 | |
| Sodium carboxymethyl cellulose | 0.85 | |
| Sodium N-lauroyl sarcosinate | 2.0 | |
| Dicalcium phosphate dihydrate | 47.0 | |

-continued

|  | Parts |
|---|---|
| Calcium carbonate | 5.0 |
| Sodium saccharine | 0.2 |
| Flavoring oil including oil of peppermint | 0.8 |
| Water | Q.S. to 100 |

This dentifrice is stable and does not separate even after accelerated aging for 9 weeks at 49° C. When the amount of ethanol is 2.5 parts, the dentifrice is also stable against separation. When ethanol is omitted, the dentifrice quickly separates into solid and liquid phases. Separation also occurs even if 1.0 part of hydrated alumina is present when ethanol is omitted.

We claim:

1. A process of preventing the separation into liquid and solid phases of an antibacterial dentifrice comprising forming the antibacterial dentifrice by adding to a single phase vehicle mass which comprises solids and liquids and which contains about 0.01–5% by weight of flavoring oil and about 0.015–2% by weight of phosphate ion, as an antibacterial agent, 1,6-di-(p-chlorophenyl biguanido) hexane, in amount to provide about 0.01–5% by weight of the free base and about 2.5–10% by weight of ethanol to prevent phase separation.

2. The process of preventing separation into liquid and solid phases of an antibacterial dentifrice as claimed in claim 1 wherein said ethanol is present in amount of about 2.5–5% by weight.

3. The process of preventing separation into liquid and solid phases of an antibacterial dentifrice as claimed in claim 1 wherein said vehicle solids include gelling agent and water-insoluble, dentally acceptable polishing agent and said vehicle liquids include water, humectant and flavoring oil.

4. The process of preventing separation into liquid and solid phases of an antibacterial dentifrice as claimed in claim 3 wherein said water-insoluble, dentally acceptable polishing agent is a phosphate salt.

5. The process of preventing separation into liquid and solid phases of an antibacterial dentifrice as claimed in claim 1 wherein sodium N-lauroyl sarcosinate is present in said vehicle.

* * * * *